United States Patent
Aiken

(10) Patent No.: US 7,126,032 B1
(45) Date of Patent: Oct. 24, 2006

(54) PURIFICATION OF GLYCERIN

(75) Inventor: John E. Aiken, Monroeville, PA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 11/387,654

(22) Filed: Mar. 23, 2006

(51) Int. Cl.
*C07C 29/80* (2006.01)
*C07C 29/82* (2006.01)
*C07C 29/88* (2006.01)

(52) U.S. Cl. .................................. 568/869; 568/868
(58) Field of Classification Search ................. 568/869, 568/868
See application file for complete search history.

(56) References Cited

U.S. PATENT DOCUMENTS

| | | | |
|---|---|---|---|
| 2,234,400 A | 3/1941 | Evans et al. |
| 2,615,924 A | 10/1952 | Reents |
| 2,741,638 A | 4/1956 | Blair et al. |
| 2,772,207 A | 11/1956 | Frankel et al. |
| 5,424,467 A | 6/1995 | Bam et al. |
| 6,262,285 B1 | 7/2001 | McDonald |

2004/0074760 A1 4/2004 Portnoff et al.

OTHER PUBLICATIONS

Glycerine and Intermediates, by Robert G. Muller, Dec. 1969; pp. 275, 277, 279, 289, 381, 382, 383, 384, 385, 386, 387, 388.
Figure 3.4. Detailed Stand-Alone Biodiesel Process Flow Diagram; 1991.
Ullmann's Encyclopedia of Industrial Chemistry, by Barbara Elvers, Stephen Hawkins, Michael Ravenscroft, James F. Rounsaville and Gail Schulz; pp. 480, 481, 482, 483, 488, 489, 1993.

*Primary Examiner*—Elvis O. Price
(74) *Attorney, Agent, or Firm*—Robert A. Koons, Jr.; Matthew P. McWilliams; Drinker Biddle & Reath LLP

(57) ABSTRACT

A process for purifying glycerin recovered as a byproduct of biodiesel production comprises heating a glycerin effluent stream containing a low molecular weight alcohol, water and fatty acid esters of the low molecular weight alcohol to cause transesterification of the fatty acid esters to glycerides and additional low molecular weight alcohol. The reaction mixture is sparged with nitrogen to help remove water and low molecular weight alcohol, which drives the transesterification reaction towards glyceride formation. A wash water stream may also be added to the recovered glycerin stream from biodiesel production. Either before or following the transesterification reaction, an oil layer can be separated from the recovered glycerin stream by reducing the pH of the stream to below 7. Following separation of the oil layer and transesterification the glycerin stream is flash distilled to separate glycerin from water, salts, and glycerides.

20 Claims, 1 Drawing Sheet

PURIFICATION OF GLYCERIN

FIELD OF THE INVENTION

The present invention relates to the field of purification of organic effluents recovered from industrial processes. More particularly, the present invention relates to the purification of glycerin recovered from a process for the manufacture of fatty acid alkyl esters.

BACKGROUND OF THE INVENTION

The main process sources for glycerin production have been high-pressure hydrolysis, transesterification of fats and oils to produce methyl ester and a glycerin byproduct, and saponification. Processing to produce refined glycerin of greater than 99.5% purity depends substantially on the type of impurities in the crude. Both pre-treatment and refining steps are typically necessary. With hydrolysis, the starting crude glycerin is likely to be nearly 85% water, hence multi-stage evaporators constructed of stainless steel are needed just for concentration. Other starting crude materials have high salt content and frequently employ thin-film distillation. A summary containing some common purification processes is provided in Ullman's Encyclopedia of Chemical Technology, Vol. A-12, pages 480–483.

As a result of the continuing rise in the cost of fossil fuels, there has been an increasing interest in biodiesel fuels as a supplement to or replacement for traditional fossil fuel sources. Biodiesel processing involves the production of alkyl esters of long chain fatty acids by reacting the source acid with a low molecular weight alcohol, such as methanol. A traditional process for manufacturing fatty acid alkyl esters involves the transesterification of triglycerides using methanol, in the presence of an alkali catalyst. In addition to the desired fatty acid alkyl esters, this process produces an effluent stream comprising glycerin (glycerol), excess alcohol, water, alkyl esters and a mixture of mono, di and triglycerides resulting from the transesterification step. The rapid worldwide expansion in the production of biodiesel fuel since 2000 is creating a fast growing supply of byproduct crude glycerin. This byproduct crude material may typically be 86–92 percent glycerol (glycerin) with methanol being the primary contaminant. The decanted glycerin is likely to be combined with a wash water stream from the biodiesel purification, and that aqueous stream can be expected to contain significant amount of methanol, glycerol, and sodium or potassium salts. Some common pretreatment steps are depicted in a process flow diagram for a biodiesel process found on page 50, FIG. 3.4, of the study report "Economic Feasibility of Producing Biodiesel in Tennessee".

The methanol needs to be recovered for recycle to the biodiesel process, but water content should be relatively low. Evaporation of the methanol can be accomplished under vacuum conditions and utilizing falling film evaporators, but it is likely to be accompanied by a considerable amount of the water coming from the wash-water stream. Alternatively, as illustrated in the aforementioned flow diagram, the methanol can be separated from the water and glycerin using a distillation column. The column bottoms then undergo a phase separation wherein unwanted fatty matter is skimmed off. The aqueous glycerin stream then undergoes evaporation of much of the water in falling film evaporators in series to obtain about an 80–89 percent glycerin material. All of these pretreatment and recovery steps involve expensive custom-made equipment even before the refining begins. As shown in Ullman's, a practical refining scheme would be a wiped-film evaporator to produce a salt-free vapor stream feed that feeds into a vacuum distillation column. The product glycerin is removed as a side-draw and a recycle glycerin stream is taken off of one overhead condenser with an aqueous stream condensed subsequent to that.

Much of prior literature references on purification of glycerin, such as U.S. Pat. Nos. 2,615,924, 2,741,638, and 2,772,207, are aimed at dilute aqueous solutions such as those resulting from fermentation and hydrolysis. Furthermore, U.S. Pat. No. 2,234,400 describes purification after concentration to 80% comprising one or more steam distillations followed by treatment with activated carbon or the like to effect decolorization. Even then, ester-type impurities are still present.

U.S. Pat. No. 4,655,879 describes an approximately 10-step process comprising alkalizing in the presence of air, evaporating in a thin-film evaporator, redistillation of the residue, rectification in a low-pressure-drop column with reboiling in a falling-film evaporator, main product removal as a liquid sidestream, with carbon treatment for color removal.

In these references, methanol was not present, or not mentioned, as a constituent in the crude feed.

It would therefore be desirable to provide a low cost efficient process for purification of glycerin recovered from fatty acid alkyl ester processes, such as the manufacture of biodiesels. Such a process would also provide an efficient low cost means for recovering alcohol from the process for recycle to biodiesel production. In addition, it is desirable to utilize predominately commonly available equipment such as might be available from idle facilities or surplus equipment previously used for other purposes. The object of this invention is to provide a simple, low-cost process for purifying glycerin byproduct from biodiesel production integrated such as to efficiently recycle methanol and accept wash water from the biodiesel process.

SUMMARY OF THE INVENTION

The present invention provides a process for purifying glycerin recovered from a fatty acid alkyl ester process, such as the production of biodiesel fuel.

According to one embodiment of the invention, a batch process for purifying glycerin from biodiesel production comprises providing a crude glycerin stream recovered from fatty acid alkyl ester production. The crude glycerin stream comprises glycerin, at least one low molecular weight alcohol, at least one glyceride, at least one fatty acid ester of the alcohol and water. The crude glycerin stream is heated to a temperature of from about 125° C. to about 160° C. so that at least a portion of the at least one fatty acid alkyl ester contained in the crude glycerin stream undergoes a transesterification with glycerin to produce additional amounts of the alcohol and additional glyceride. The crude glycerin stream is sparged with nitrogen, thereby stripping most of the alcohol and a portion water from the crude glycerin stream, to produce a glycerin effluent stream comprising glycerin, at least one glyceride and water, and also yielding a condensed alcohol stream overhead with less than 5 percent water. An aliquot of wash water from the biodiesel cleanup may then be added followed by additional nitrogen sparging at about 125° C. to about 160° C. until the water content in the glycerin material is approximately 5 percent. After skimming off unwanted organic matter that is not glycerin (MONG), the glycerin effluent stream is distilled in a flash distillation column wherein water and glycerin are vaporized and removed as an overhead stream.

According to an alternative continuous embodiment of the invention, the process comprises providing a crude glycerin stream recovered from fatty acid alkyl ester production. The crude glycerin stream comprises glycerin, at least one low molecular weight alcohol, at least one glyceride, water and perhaps at least one fatty acid ester of a low molecular weight alcohol. The crude glycerin stream is heated to a temperature in the range of about 125° C. to about 160° C. The crude glycerin stream is fed to a first reactor maintained at about 125° C. to about 160° C., wherein at least a portion of the at least one fatty acid alkyl ester contained in the crude glycerin stream undergoes a transesterification with glycerin to produce additional amounts of the alcohol and additional glyceride. The first reactor is sparged with nitrogen, thereby stripping a portion of the alcohol and water from the crude glycerin stream, producing a first glycerin effluent stream. The first glycerin effluent stream from the first reactor is mixed with a process water stream containing at least one low molecular weight alcohol and glycerin. The mixed glycerin effluent and water stream are transferred to a second reactor maintained at about 120° C. to about 160° C. The second reactor is sparged with nitrogen, thereby stripping at least a portion of the alcohol and a portion of the water from the mixed crude glycerin and water stream, to produce a second effluent stream comprising glycerin, at least one glyceride and water. In the second reactor, some of the glyceride and residual fatty acid ester may undergo hydrolysis to form more glycerin and some free fatty acid. The second glycerin effluent stream is distilled in a flash distillation column wherein water and glycerin are vaporized and removed as an overhead stream. The overhead stream is first partially condensed to separate purified glycerin from water vapor, which is subsequently removed to a secondary condenser where it is condensed.

According to preferred embodiments of both the batch and continuous processes, a side stream comprising glycerin vapor is removed and condensed to recover a second purified glycerin product, which may be combined with the glycerin recovered from the overhead stream.

The streams thus recovered are optionally subjected to a further treatment by passing through at least one bed of a sorbent. The streams can be treated separately, but are preferably combined prior to treatment. Exemplary sorbents that can be used for the treatment are activated carbon, ion-exchange resins and molecular sieves.

DETAILED DESCRIPTION OF THE INVENTION

Figure 1:
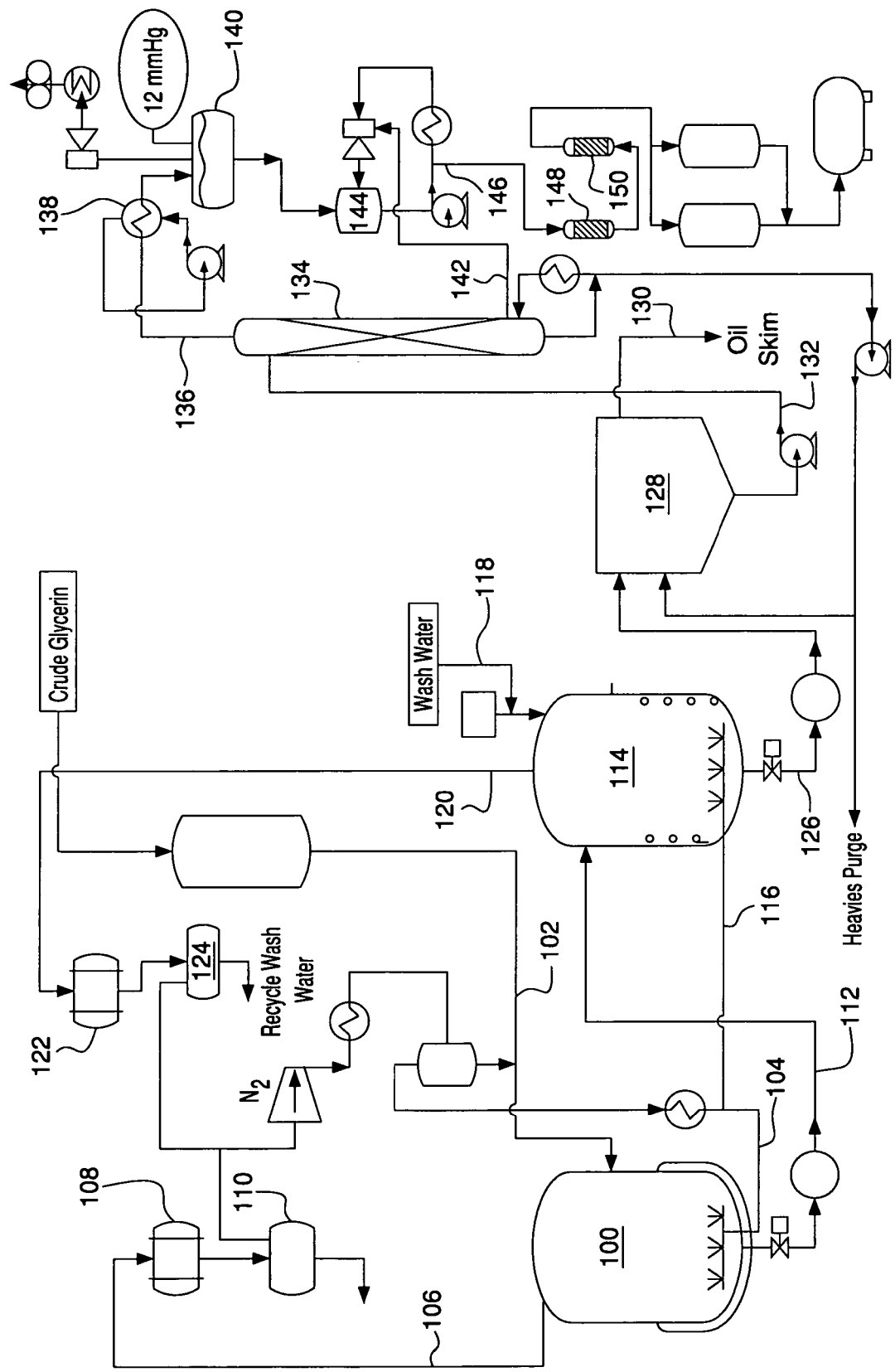
FIG. 1 Illustrates an embodiment of a continuous process glycerin recovery system according to the current invention.

The present invention provides a process for purification of glycerin recovered from a fatty acid alkyl ester process, such as a biodiesel production process.

Traditional methods for producing fatty acid alkyl esters involve supplying long chain fatty acids in the form of triglycerides (natural oils). The triglycerides are transesterified with alcohols, generally low molecular weight alcohols, for example methanol, ethanol, n-propanol and isopropanol, in the presence of a heterogeneous or alkyloxide catalyst to produce fatty acid alkyl esters and a mixture of mono and diglycerides and glycerin (glycerol). Generally, methanol is the alcohol of choice in such processes. However, it is contemplated that any alcohol or mixture of alcohols may be used in such a process.

Although such processes are run using an excess of the alcohol or alcohols of interest, the transesterification generally does not proceed to absolute completion during the reaction period. The resulting glycerin effluent stream separated from the fatty acid alkyl ester product therefore contains a mixture of mono, di and possibly triglycerides, as well as excess alcohol, water and some fatty acid alkyl esters that are entrained with the effluent stream. In addition, the effluent stream sometimes contains residual catalyst or salts.

In addition to the glycerin effluent stream, a number of fatty acid alkyl ester processes make use of water washes to remove residual catalyst, alcohol and glycerin from the product fatty acid alkyl ester.

The process according to the current invention provides an efficient method for purifying glycerin from both the glycerin effluent stream and the process water washes, where such washes are used.

By using reactive stripping according to the invention, the entrained fatty acid alkyl esters are converted to alcohols, which are recovered for recycle, and glycerides, which are higher boiling than fatty acid alkyl esters, and hence easier to separate from glycerin.

An embodiment of the process will now be described with reference to the exemplary FIG. 1. Because methanol is typically the alcohol of choice, this embodiment will be described in terms of a process for the production of fatty acid methyl esters (FAME). It will be recognized by those skilled in the art however, that the present invention will be applicable to any number of alcohols, or mixtures thereof.

Referring to FIG. 1, a preheated crude glycerin stream is introduced to tank 100 via feed line 102. In the preferred mode of operation, sulfuric acid is added to the crude glycerin to bring the pH just below 7. According to the exemplary embodiment, in addition to glycerin, the crude glycerin stream will contain residual mono, di and triglycerides, methanol, water and perhaps FAME. The crude glycerin stream is preferably preheated to a temperature of from about 125° C. to about 160° C. The tank 100 is maintained at an operating temperature of from about 125° C. to about 160° C. Preferably, the tank is not equipped with any heating, but maintains the proper operating temperature by the continuous flow of preheated crude glycerin stream. However, the tank may be equipped with heating if desired. A nitrogen sparge is introduced to tank 100 via line 104. The flow rate of nitrogen to tank 100 is from about 3 percent to about 20 percent by weight based on the feed rate of crude glycerin to the tank 100. The nitrogen sparge provides the necessary agitation to the tank and helps to volatilize methanol and water in the crude glycerin stream at relatively moderate temperatures. Preferably the tank 100 is not equipped with any internal agitation mechanism, but instead relies on the agitation developed by the nitrogen sparge. However, the tank 100 may be equipped with an internal agitation mechanism and operated under vacuum, if desired.

In tank 100 the entrained FAME undergoes transesterification with glycerin to produce glycerides and methanol. At least a portion of the methanol produced, and at least a portion of the methanol and water contained in the glycerin stream itself are volatilized by the heat and nitrogen sparge, and are removed via line 106 and condensed and collected at condenser 108 and separator 110 respectively. Removal of the methanol acts to drive the transesterification reaction to glycerides to near completion.

Still referring to FIG. 1, a first glycerin effluent stream is removed from tank 100 via line 112 and transferred to second tank 114. In addition to glycerin, the first glycerin effluent stream comprises glycerides, methanol and water, and may potentially contain residual FAME as well. Optionally, a process water wash stream from the FAME process is introduced to tank 114 via line 118. The process wash water will contain glycerin, glycerides, methanol and may contain small amounts of FAME.

The second tank 114 is maintained at an operating temperature of about 120° C. to about 160° C. Again, preferably tank 114 is not equipped with any heating, but rather maintains the appropriate operating temperature by the continuous flow of the hot first glycerin effluent stream. The second tank 114 may be equipped with internal heating if desired however. A nitrogen sparge, preferably heated, is introduced to tank 114 via line 116. The flow rate of nitrogen to tank 114 is from about 2 percent to about 15 percent by weight based on the feed rate of crude glycerin to the tank 114. The nitrogen sparge provides the necessary agitation to the tank and helps to volatilize methanol and water in the crude glycerin stream. Preferably the tank 114 is not equipped with any internal agitation mechanism, but instead relies on the agitation developed by the nitrogen sparge. However, the tank 114 may be equipped with an internal agitation mechanism if desired.

In the second tank, any residual methanol from the first tank 100, as well as methanol introduced with the wash water stream is substantially removed leaving behind the glycerin contained in the wash water, and adjusting the water content of the glycerin stream to a desired range, preferably about 5 percent. The methanol and water contained in the glycerin and process water streams themselves are volatilized by the heat and nitrogen sparge, and are removed via line 120 and condensed and collected at condenser 122 and separator 124 respectively. In the preferred method of operation, the post-condenser nitrogen streams from 110 and 124 are recirculated via a common booster blower. Each of the two reactors is sized to provide intimate contact of the liquid and nitrogen with sufficient cross section area to preclude any significant entrainment into the gas stream. Meeting these requirements will typically result in at least 30 minutes of residence time. Preferably, all of the remaining methanol is removed, however, a fraction of the methanol may remain in the glycerin stream. In a preferred embodiment, approximately 5 percent water remains in the glycerin stream.

A second glycerin effluent stream is removed from tank 114 via line 126. In addition to glycerin, the second glycerin effluent stream comprises glycerides and water. The second glycerin effluent stream may also contain some residual methanol, preferably 0.5 percent by weight or less, more preferably no methanol. The second glycerin effluent stream preferably contains approximately 5 percent water by weight. The residual water aids in the subsequent flash distillation step. Also preferably, the second glycerin effluent stream contains no residual FAME. However, trace amounts of FAME may remain in the second glycerin effluent stream.

Still referring to FIG. 1, according to the exemplary embodiment, the second glycerin effluent stream is passed to third tank 128 which may serve as a feed tank to the flash distillation. Also optionally, tank 128 may serve as a decanter to remove an oil layer which will separate from the glycerin effluent stream after lowering the pH below 7 either before or after the transesterification reaction. Where an oil layer is present, it may be skimmed from the glycerin layer and removed via line 130. In the exemplary embodiment, this third tank also receives the recycle stream from the bottom of the flash distillation step. According to an alternative embodiment of the invention, not shown, the oil separation step may be performed prior to feeding the crude glycerin stream to the first tank, but after reducing the pH to less than 7.

Referring back to FIG. 1, according to the exemplary embodiment a third glycerin effluent stream is removed from the third tank 128 via line 132 and sent to stripping column 134. The stripping column preferably comprises a short packed column above a steam-heated reboiler. According to a preferred embodiment, the third glycerin effluent stream is preheated prior to the stripping column 134 to partially volatilize the glycerin and water in the stream. Where no water stream is added to the second tank 114, live steam may be added to the glycerin feed to the stripping column to aid in vaporizing glycerin. The stripping column 134 is maintained at a temperature and vacuum sufficient to volatilize most of the glycerin and all of the water in the stream, typically a temperature of about 185° C. and a pressure of about 5 to about 20 mm Hg. A portion of the glycerin and water are vaporized in the stripping column and removed as an overhead stream via line 136. Preferably there is no reflux returned to the column from the overheads. Glycerin in the overhead stream is condensed at a first condenser 138 and collected at separator 140, which are maintained at approximately the same pressure as the stripping column 134 and from about 82° C. to about 116° C. The water, which remains vaporized is removed to a secondary condenser, recovered and sent to waste water.

The bottoms stream from the stripping column, which comprises glycerides and other heavy products may be recycled to the third tank 128. Alternatively, if the bottoms stream from the stripping column contains a significant amount of glycerides, a portion of it may be recycled to the FAME process. The distillation process is designed to produce about 10% to about 20% of the glycerin feed stream as bottoms. This minimizes residence time in the reboiler, which in turn minimizes degradation and by-product formation. A portion of the bottoms stream can be purged continuously or intermittently as deemed necessary to prevent the excessive buildup of salts and glycerides. Because the purge is water soluble, disposal via a wastewater treatment plant may be most expedient and economical.

Still referring to FIG. 1, according to a preferred embodiment, in addition to the vapor overheads, a vapor side stream 142, comprising glycerin is withdrawn from the stripping column 134. Also according to a preferred embodiment, the glycerin side stream 142 and the condensed glycerin from first condenser 138 may be combined in tank 144. The combined stream may then be sent via line 146 to sorbent beds 148 and 150. The sorbent beds remove color and trace impurities from the purified glycerin. Non-limiting examples of materials that may be used to pack the sorbent beds include activated carbon, ion-exchange resins and molecular sieves.

In addition to the continuous process described above, the process may be run as a batch process using the same configuration described in FIG. 1. Alternatively, in batch mode as few as a single vessel may be used to accomplish all of the steps described for tanks one, two and three above. In either case the distillation step should be run in continuous mode to minimize the heating time for the crude glycerin stream.

The exemplary embodiment of the process as illustrated in FIG. 1 was modeled using the ASPEN Plus™ software available from Aspen Technologies, Inc. The results of the simulation are shown in Table 1 below.

TABLE 1

| Component | Crude Glycerin Mass lb/hr. | Crude Glycerin Wt. % | Tank 1 Effluent Mass lb/hr. | Tank 1 Effluent Wt. % | Recovered Methanol Mass lb/hr. | Recovered Methanol Wt. % | Stripping Column Feed Mass lb/hr. | Stripping Column Feed Wt. % | Recovered Glycerin Mass lb/hr. | Recovered Glycerin Wt. % | Column Bottoms Mass lb/hr. | Column Bottoms Wt. % |
|---|---|---|---|---|---|---|---|---|---|---|---|---|
| Water | 83 | 1.00 | 39 | 0.53 | 46 | 4.67 | 409 | 5.32 | 26.0 | 0.416 | 0 | 0.00 |
| CH$_3$OH | 996 | 12.00 | 79 | 1.08 | 917 | 93.10 | 30 | 0.39 | 0.1 | 0.002 | 0 | 0.00 |
| Glycerin | 7196 | 86.70 | 7167 | 98 | 22 | 2.23 | 7190 | 93.60 | 6224.0 | 99.576 | 1102 | 87.46 |
| FAME | 21 | 0.25 | 0 | 0.00 | 0 | 0.00 | 0 | 0.00 | 0 | 0.00 | 0 | 0.00 |
| Heavies* | 4 | 0.05 | 30 | 0.41 | 0 | 0.00 | 53 | 0.69 | 0.4 | 0.006 | 158 | 12.54 |
| Total | 8300 | 100.00 | 7315 | 100.00 | 985 | 100.00 | 7682 | 100.00 | 6250.5 | 100.00 | 1260 | 100.00 |

*Includes Glycerides

The crude glycerin stream used as the basis for the model has a composition that is typical for crude glycerin streams coming from the production of fatty acid methyl ester production for biodiesel. The crude glycerin stream is approximately 86.7 weight percent glycerin, with most of the balance, about 12.0 percent, being methanol. Modeling the process according to the exemplary embodiment using this typical feed results in a predicted effluent stream from the first tank containing essentially no FAME and a significantly reduced content of methanol, approximately 1.08 weight percent. This demonstrates that the transesterification of FAME in the first tank essentially goes to completion and that methanol is efficiently removed from the glycerin stream. The model also demonstrates that methanol can be recovered overhead from the first tank with an acceptable water content of less than 5 weight percent. The feed to the stripping column, coming from the second tank via the decanter shows the glycerin stream having an adjusted water content and further reduced methanol content, obtained by addition of a wash water stream and further stripping of water and methanol in the second tank. The composition of the wash water will depend on many factors, such as the efficiency of the upstream phase separation, as well as catalyst and methanol concentrations used in the biodiesel transesterification reaction. The wash water stream will most likely be the concentrated aqueous product from a countercurrent multi-stage washing operation, whether done continuously or batchwise, wherein the incoming organic stream first contacts the most concentrated water stream. For modeling purposes, the methanol and glycerin were both assumed to be less than 2 weight percent in the wash water. In practice, conditions such as temperature and sparging rate in the second vessel would be adjusted as needed to have the water content close to 5 percent in its effluent. The model further predicts a recovered glycerin stream from the flash distillation having a purity of greater than 99.5 percent, with most of the balance being water. The column bottoms, still containing a significant amount of glycerin, can be continuously or intermittently purged in part with most being recycled to the decanter.

EXAMPLE

The process according to the current invention was modeled experimentally on a bench scale. The only differences from the modeled process and the industrial scale process described above were that only a single reactor was used, batchwise, on the bench scale, as opposed to two in series and continuous mode for the process described above, and that the distillation step was done in a wiped film evaporation unit as opposed to a short packed column, following completion of the batch stripping and conversion of FAME to glycerides.

Approximately 1.5 gallons of glycerin byproduct was obtained from a biodiesel pilot plant. This material is believed to be typical of byproduct streams from biodiesel production. A small amount of biodiesel fuel floating on top of the glycerin byproduct was decanted away. The crude glycerin had an initial pH of approximately 11.6. After adjusting the pH of a portion of the crude glycerin to approximately 5.8, approximately 1000 grams of the pH adjusted material was charged to a 1.5 liter resin kettle. The crude glycerin was heated to about 153° C. with nitrogen sparging for a period of approximately 1.5 hours. Over this time 63.2 grams of volatiles were collected overhead. The distillate had a density of 0.83 g/mL, indicating that it was mostly methanol. The cooled contents were charged to a glass separatory funnel and allowed to phase separate over night. On separating 593.4 grams of a lower product phase was collected, and 272.6 grams of an upper phase was collected.

Another batch was prepared in a similar manner, except that the pH was adjusted to only 6.8 this time and a phase separation was performed prior to charging to the resin kettle.

Water was added to both lower phases to a concentration of about 5 weight percent. The higher pH batch had to be filtered to remove solids that had precipitated. The lower phases were then combined for the distillation.

The continuous-mode distillation was performed using a 4-inch diameter Pope wiped film evaporator to simulate the vacuum conditions that are expected to be used in practice and the vapor side draw. The upper zone of the wiped film evaporator was maintained at 156 to 160° C. and the lower zone was maintained at 173 to 176° C. The absolute pressure in the system was maintained at 7 to 9 mm Hg. The crude glycerin feed was pumped in continuously at rates ranging from 3 to 10 mL/min over the course of more than 3 hours. A first product cut, simulating the side product cut, was collected in a receiver attached to the wiped film evaporator where product from the internal condenser is collected. A second cut was obtained by condensing a vapor stream from the wiped film evaporator at a first condenser after the wiped film evaporator, which was filled with hot water to condense out glycerin. This simulated the overhead glycerin fraction to be collected. Finally, water was condensed out of the vapor stream using a cold trap condenser cooled with water ice. Some of the water vapor appeared to get carried over into the vacuum pump.

The side product cut amounted to 194.5 grams of a lightly amber colored product, which had a density of 1.259. The overhead product cut was 220.7 grams of a water white product, which had a density of 1.256. The specific gravity for pure glycerin is 1.261. A total of 386.3 grams of evaporator bottoms were also collected. The total recovery represented by the side and overhead product cuts was only 51%. This is likely due to too high a feed rate initially and lower than desirable temperature during the distillation. Also, it should be noted that the process design calls for recycle of the distillation bottoms.

The invention has thus been described with reference to exemplary drawings and a working example. The novel process according to the current invention utilizes common, simple equipment and allows for low energy recovery of a purified glycerin stream. In addition, the process allows for recovery of greater than 90 percent of the low molecular weight alcohol from the crude glycerin and process water streams, most of it as a relatively low-water material suitable for recycle as is.

What is claimed is:

1. A process for purifying glycerin recovered from a fatty acid alkyl ester process, comprising:
    providing a crude glycerin stream recovered from fatty acid alkyl ester production, the crude glycerin stream comprising: glycerin, at least one low molecular weight alcohol, at least one glyceride, at least one fatty acid ester of a low molecular weight alcohol and water,
    heating the crude glycerin stream to a temperature of from about 125° C. to about 160° C.,
    feeding the crude glycerin stream to a first reactor maintained at about 125° C. to about 160° C., wherein at least a portion of the at least one fatty acid alkyl ester contained in the crude glycerin stream undergoes a transesterification with glycerin to produce additional amounts of the at least one low molecular weight alcohol and additional glyceride,
    in the first reactor, sparging the crude glycerin stream with nitrogen, thereby stripping a portion of the at least one low molecular weight alcohol and water from the crude glycerin stream, to produce a first glycerin effluent stream,
    feeding the first glycerin effluent stream from the first reactor to a second reactor maintained at about 120° C. to about 160° C.,
    in the second reactor, sparging the first effluent stream with nitrogen, thereby stripping the at least a portion of the at least one low molecular weight alcohol and a portion of the water, to produce a second effluent stream comprising glycerin, at least one glyceride and water;
    distilling the second glycerin effluent stream in a flash distillation column wherein water and glycerin are vaporized and removed as an overhead stream.

2. The process according to claim 1, further comprising, adding a water stream containing at least one low molecular weight alcohol and glycerin, to the first glycerin effluent stream, wherein
    additional amounts of the at least one low molecular weight alcohol and water are stripped out in the second reactor.

3. The process according to claim 1, further comprising:
    condensing a glycerin fraction from the distillation overhead stream to separate purified glycerin from water, and passing the remaining vapor thus separated to a secondary condenser where it is recovered.

4. The process according to claim 1, further comprising prior to distilling the second glycerin effluent stream, but after reducing the pH below 7, separating the second glycerin effluent stream into a top layer comprising oil and fatty acid and a bottom layer comprising glycerin, water, and at least one glyceride,
    wherein the bottom layer is the stream to be distilled.

5. The process according to claim 3, further comprising:
    removing a sidestream comprising glycerin vapor from the flash distillation column, and condensing the sidestream.

6. The process according to claim 1, wherein the first reactor is sparged with nitrogen at a rate of from about 3 percent to about 20 percent by weight of the crude glycerin stream feed rate to the first reactor, and the second reactor is sparged with nitrogen at a rate of from about 2 percent to about 15 percent by weight of the crude glycerin stream feed rate to the second reactor.

7. The process according to claim 1, further comprising, preheating the second glycerin effluent stream prior to the distillation column to partially vaporize glycerin and water in the second effluent stream.

8. The process according to claim 5, further comprising, combining the condensed sidestream product and condensed overhead glycerin fraction to form one liquid stream, and
    passing the one liquid stream over at least one bed of sorbent.

9. The process according to claim 2, wherein the first glycerin effluent stream and water stream are mixed prior to being fed to the second reactor.

10. The process according to claim 2, wherein
    in the second reactor a portion of the glycerides and fatty acid esters are hydrolyzed to produce additional glycerin and free fatty acids.

11. The process according to claim 1, further comprising
    prior to heating the crude glycerin stream to a temperature of from about 125° C. to about 160° C. in the first reactor, but after reducing the pH below 7, separating the crude glycerin stream into a top layer comprising oil and fatty acid and a bottom layer comprising glycerin, at least one low molecular weight alcohol, at least one glyceride, at least one fatty acid ester of a low molecular weight alcohol and water, wherein
    the bottom layer is the stream to be heated to about 125° C. to about 160° C.

12. The process according to claim 3, wherein the distillation bottoms are predominately recycled to an upstream step with a partial purge to prevent excessive accumulation of salts and other impurities.

13. A process for treating glycerin recovered from a fatty acid alkyl ester process, comprising:
    providing a crude glycerin stream recovered from fatty acid alkyl ester production, the crude glycerin stream comprising: glycerin, at least one low molecular weight alcohol, at least one glyceride, at least one fatty acid ester of a low molecular weight alcohol and water,
    heating the crude glycerin stream to a temperature of from about 125° C. to about 160° C. so that at least a portion of the at least one fatty acid alkyl ester contained in the crude glycerin stream undergoes a transesterification with glycerin to produce additional amounts of the alcohol and additional glyceride;
    sparging the crude glycerin stream with nitrogen, thereby stripping a portion of the alcohol and water from the crude glycerin stream, to produce a glycerin effluent stream comprising glycerin, at least one glyceride and water;
    distilling the glycerin effluent stream in a flash distillation column wherein water and glycerin are vaporized and removed as an overhead stream.

14. The process according to claim 13, further comprising, adding a water stream containing at least one alcohol and glycerin, to the crude glycerin stream;

wherein additional amounts of the at least one low molecular weight alcohol and water are stripped out.

15. The process according to claim 13, further comprising prior to distilling the glycerin effluent stream, but after reducing the pH below 7, separating the glycerin effluent stream into a top layer comprising oil and fatty acid and a bottom layer comprising glycerin, water, and at least one glyceride, wherein the bottom layer is the stream to be distilled.

16. The process according to claim 13, further comprising, preheating the glycerin effluent stream prior to the distillation column to partially vaporize glycerin and water in the effluent stream.

17. The process according to claim 13, further comprising:

condensing a glycerin fraction from the overhead stream to separate purified glycerin from water, and passing the remaining vapor thus separated to a secondary condenser where it is recovered.

18. The process according to claim 17, further comprising:

removing a sidestream comprising glycerin vapor from the flash distillation column, and condensing the sidestream.

19. The process according to claim 18, further comprising, combining the condensed sidestream product and condensed overhead glycerin fraction to form one liquid stream, and passing the one liquid stream over at least one bed of sorbent.

20. The process according to claim 13, further comprising prior to heating the crude glycerin stream to a temperature of from about 125° C. to about 160° C., but after reducing the pH below 7, separating the crude glycerin stream into a top layer comprising oil and fatty acid and a bottom layer comprising glycerin, at least one low molecular weight alcohol, at least one glyceride, at least one fatty acid ester of a low molecular weight alcohol and water, wherein the bottom layer is the stream to be heated to about 125° C. to about 160° C.

* * * * *